United States Patent
Yasukawa et al.

(10) Patent No.: US 8,855,266 B2
(45) Date of Patent: Oct. 7, 2014

(54) X-RAY STRESS MEASUREMENT APPARATUS

(75) Inventors: Shoichi Yasukawa, Hino-shi (JP); Tomoyuki Iwata, Hamura-shi (JP)

(73) Assignee: Rigaku Corporation, Akishima-Shi, Tokyo (JP)

( * ) Notice: Subject to any disclaimer, the term of this patent is extended or adjusted under 35 U.S.C. 154(b) by 291 days.

(21) Appl. No.: 13/544,161

(22) Filed: Jul. 9, 2012

(65) Prior Publication Data

US 2013/0039469 A1 Feb. 14, 2013

(30) Foreign Application Priority Data

Aug. 8, 2011 (JP) ................. 2011-173472

(51) Int. Cl.
G01N 23/04 (2006.01)
G01N 23/207 (2006.01)
G01L 1/25 (2006.01)

(52) U.S. Cl.
CPC ........ *G01N 23/207* (2013.01); *G01N 2223/607* (2013.01); *G01N 2223/3303* (2013.01); *G01N 2223/408* (2013.01); *G01L 1/25* (2013.01)
USPC .......................................................... 378/63

(58) Field of Classification Search
USPC ................................ 378/62, 63, 98, 98.5, 207
See application file for complete search history.

(56) References Cited

U.S. PATENT DOCUMENTS

| 6,750,451 | B2 | 6/2004 | Koguchi et al. | |
| 7,705,267 | B2 * | 4/2010 | Heyl | 219/121.68 |
| 2005/0099423 | A1 | 5/2005 | Brauss | |
| 2007/0024622 | A1 | 2/2007 | Brauss | |

FOREIGN PATENT DOCUMENTS

| JP | 03-018733 A | 1/1991 |
| JP | 03-059449 A | 3/1991 |
| JP | 2002-214164 A | 7/2002 |
| JP | 2005-091046 A | 7/2005 |
| JP | 2007-519893 A | 7/2007 |
| JP | 2009-300232 A | 12/2009 |

* cited by examiner

*Primary Examiner* — Irakli Kiknadze
(74) *Attorney, Agent, or Firm* — Buchanan Ingersoll & Rooney PC

(57) ABSTRACT

An X-ray stress measurement apparatus having: a camera for producing an optical image of a sample; a display for displaying the optical image; an input device capable of inputting positions on a display screen; an X-ray source for generating an X-ray; a table for moving the sample; an X-ray detector for detecting an X-ray exiting the sample; a measurement program for determining the measurement positions of the sample on the basis of the positions indicated by the input device, and measuring the determined measurement positions of the sample; a stress computation program for computing the stress at the measurement positions of the sample on the basis of an output signal from the X-ray detector; and an image formation program for causing the optical image, the measurement positions of the sample, the absolute value of the stress, and the direction of the stress to be displayed on the same display screen.

12 Claims, 15 Drawing Sheets

X-RAY STRESS MEASUREMENT APPARATUS

BACKGROUND OF THE INVENTION

1. Field of the Invention

The present invention relates to an X-ray stress measurement apparatus for measuring stress remaining inside of a substance using an X-ray.

2. Description of the Related Art

Conventional measuring of stress inside of a substance using an X-ray is disclosed, for example, in Patent Citation 1. According to Patent Citation 1, it is disclosed that stress, errors, intensity ratio, peak width, and the like that have been calculated as measurement results are correlated with position information of the object to be measured (i.e., a sample), and then mapped and displayed. A mapping display refers to displaying the physical quantities, for example stress and the like, in association with the position information of the sample.

Specifically, in Patent Citation 1, measurement positions of a sample are taken in XY plane coordinates in an XYZ three-dimensional coordinate system, the material properties information such as the stress or the like (i.e., the physical quantities) are taken on the Z axis in the XYZ three-dimensional coordinate system, and a mapping display is performed (for example, FIG. 11 in Patent Citation 1).

Patent Citation 2 discloses a conventional analysis apparatus provided with a mapping function. As used in Patent Citation 2, the mapping function refers to the function of making the relationship between the scanning position and intensity of the X-ray into an image (paragraph "0002" in Patent Citation 2). Patent Citation 2 also discloses that an optical observation image of the surface of the sample together with a map image is continuously acquired by a television camera (paragraph "0017" in Patent Citation 2). The map image refers to defining the X-ray intensity information for each mapping unit area, i.e., the X-ray intensity information for every position (paragraphs "0021", "0022" in Patent Citation 2). Patent Citation 2 also discloses that an optical observation image having the same field of view as the mapping observation range is obtained at the same time (paragraph "0027" in Patent Citation 2).

Patent Citation 3 discloses a conventional X-ray apparatus provided with an input function suitable for mapping and measurement. As used in Patent Citation 3, mapping and measurement refer to setting a plurality of measurement points on a surface of a sample to be measured, and performing X-ray measurement in relation to each of the measurement points to obtain measurement data such as diffraction X-ray intensity data and the like. Patent Citation 3 discloses an apparatus capable of managing the coordinate values of measurement points on the photo screen in the same way as coordinate values on the XY stage by converting the measurement point data indicated on the photo screen (paragraph "0035" of Patent Citation 3) into coordinate values on the coordinates of the XY stage (paragraph "0037" of Patent Citation 3).

[Patent Citation 1]
   Japanese Domestic Republication No. 2007-519893
[Patent Citation 2]
   Japanese Laid-Open Patent Publication No. 2009-300232
[Patent Citation 3]
   Japanese Laid-Open Patent Publication No. 2002-214164

SUMMARY OF THE INVENTION

In the apparatus disclosed in Patent Citation 1, the measurement positions of the sample are specified by coordinates on the apparatus, and are not specified by coordinates on the sample. The measurement positions of the sample based on the coordinates on the sample must be separately entered by the user. In this method, a problem arises in which the user must check and compare the measurement positions recorded by the user and the mapping display of the material properties information, which are the measurement results, and it is difficult to comprehend the direct relationship.

Patent Citation 2 discloses that a map image is acquired by the X-ray measurements and that an optical observation image is acquired by a camera at the same time, but does not discuss how these images are displayed. That is, there is no teaching in Patent Citation 2 about a mapping display, which is an object of the present invention, i.e., associating and displaying the physical quantities such as stress and the like with the position information of the sample.

According to the apparatus disclosed in Patent Citation 3, points to be measured, which are positions at which measurement is performed, can be simply and accurately identified on a picture screen. However, in Patent Citation 3, no consideration is given to associating the data obtained by measurements with a picture screen and displaying the data in a form easily understandable by a user.

OBJECT OF THE INVENTION

The present invention was devised in view of the foregoing problems in conventional apparatuses, and an object thereof is to provide an X-ray stress measurement apparatus in which material properties information for each part of a sample can be readily, intuitively, and accurately displayed for a user.

CONFIGURATION OF THE INVENTION

An X-ray stress measurement apparatus according to the present invention comprises: optical imaging means for picking up an optical image of a sample; a display for displaying the optical image of the sample; input means capable of inputting positions on a screen of the display; an X-ray source for generating an X-ray; sample transporting means for moving the sample; X-ray detection means for detecting the X-ray exiting from the sample; measurement means (for example, the stress measurement program 20 and CPU 15 of FIG. 1) for controlling the operation of the optical imaging means, the display, the input means, the X-ray source, the sample transporting means, and the X-ray detection means, determining measurement positions of the sample on the basis of the positions indicated by the input means, and measuring the determined measurement positions of the sample; stress computation means (for example, the stress measurement program 20 of FIG. 1) for computing the stress at the measurement positions of the sample on the basis of an output signal from the X-ray detection means; and image formation means (for example, the image formation program 22 of FIG. 1) for causing the optical image of the sample, the measurement positions of the sample, the absolute value of the stress, and the direction of the stress to be displayed on the same screen of the display.

According to the X-ray stress measurement apparatus of the present invention, measurement positions are indicated in a screen by displaying an optical image of a sample on the screen of a display, an X-ray diffraction measurement is performed in relation to the measurement positions, material properties information (i.e., physical quantities) such as stress or the like is obtained, and the obtained information is linked with each of the measurement positions and displayed (i.e., a mapping display).

In the present invention, the determination of measurement positions and the display of material properties information are thus performed with the optical image of the sample as a reference. Therefore, the measurement positions relating to the sample can be quickly and accurately specified, and moreover, the relationship between the material properties information and the measurement information can be directly, i.e., intuitively comprehended. Accordingly, analysis relating to the sample can be quickly and accurately performed.

In the X-ray stress measurement apparatus according to present invention, the image formation means can display the measurement positions of the sample by dots; display the absolute value of the stress by shades of color of the dots; display positive and negative stress using a classification of the color of the dots; and display the direction of application of the stress using direction notation symbols.

In the above configuration, the image formation means can be formed by the CPU or the like for implementing predetermined functions in accordance with, for example, a predetermined program. "Positive" stress is, for example, tensile stress. "Negative" stress is, for example, compressive stress. The "direction of application" of stress is the application of the stress $\sigma_x$ in the x-direction within planar coordinates, and the application of stress $\sigma_y$ in the y-direction, which is perpendicular to the x-direction. "Direction notation symbols" are symbols for displaying the direction, for example, the letters for "$\sigma_x$" and "$\sigma_y$" themselves, the arrows expressing the direction, and other symbols.

According to this aspect of the invention, the operator can intuitively, readily, and accurately judge the state of the stress inside of the sample by viewing the display screen, i.e., the mapping display.

In the X-ray stress measurement apparatus according to the present invention, the image formation means can display the measurement positions of the sample by dots; display the absolute value of the stress by the size of the dots; display positive and negative stress using a pattern in which the dots are empty or a pattern in which the dots are filled; and display the direction of application of the stress using direction notation symbols.

According to this aspect of the invention, the operator can intuitively, readily, and accurately judge the state of the stress inside of the sample by viewing the display screen, i.e., the mapping display.

In the X-ray stress measurement apparatus according to the present invention, the image formation means can display the measurement positions of the sample by ring-shaped dots; display the absolute value of the stress by the size of the ring-shaped dots; display positive and negative stress using a difference in color of the ring-shaped dots; and display the direction of application of the stress using direction notation symbols.

According to this aspect of the invention, the operator can intuitively, readily, and accurately judge the state of the stress inside of the sample by viewing the display screen, i.e., the mapping display.

In the X-ray stress measurement apparatus according to the present invention, the image formation means can display the measurement positions of the sample using an intersection of a pair of mutually orthogonal arrows; display the absolute value of the stress using the length of the arrows; display positive and negative stress using a difference in color of the arrows; and display the direction of application of the stress using the orientation of the arrows.

According to this aspect of the invention, the operator can intuitively, readily, and accurately judge the state of the stress inside of the sample by viewing the display screen, i.e., the mapping display.

The X-ray stress measurement apparatus according to the present invention further comprises distinctive point display means. The distinctive point display means has a plurality of types of parameters for defining whether the sample is distinctive, and can perform a distinctive point display for displaying a distinctive point at a corresponding measurement position when the measurement value of the parameters is a value expressing distinctiveness. The operator can readily, quickly, and accurately ascertain the distinctive points within a sample using this configuration.

In the X-ray stress measurement apparatus according to the present invention, the measurement means can control measurement so that measurement is performed in relation to the measurement positions of the sample when the measurement positions of the sample are indicated by the input means in a state in which the optical image of the sample, the measurement positions of the sample, the absolute value of the stress, the positive and negative stress, and the direction of application of the stress are visually displayed on the display.

The operator can measure another measurement as necessary while viewing the connection between the material properties information such as $\sigma_x$ and $\sigma_y$, which are the measurement results, and the measurement positions using this configuration. That is, according to this aspect of the invention, obtained measurement results can act as feedback information for performing subsequent measurements.

DESCRIPTION OF THE PREFERRED EMBODIMENTS

Figure 1:
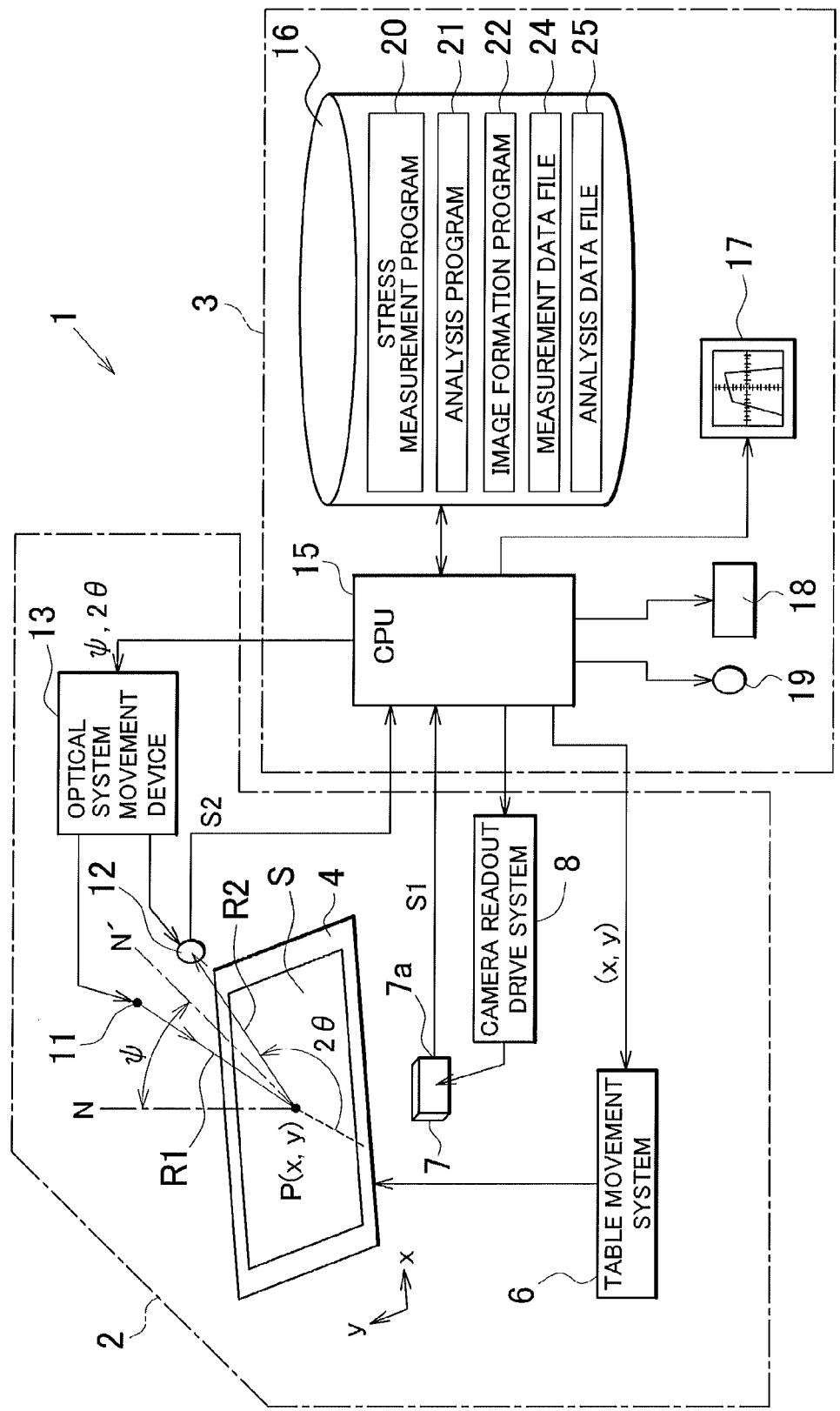
FIG. 1 is a view showing an embodiment of an X-ray stress measurement apparatus according to the present invention.

An X-ray stress measurement apparatus according to the present invention will be described below on the basis of the embodiments. It is apparent that the present invention is not limited to the embodiments. In addition, components are sometimes shown having proportions different from those of actual components in order to make the characteristic portions in the drawings attached to the present description easily understandable.

FIG. 1 shows an embodiment of an X-ray stress measurement apparatus according to the present invention. The X-ray stress measurement apparatus 1 shown here has a measurement operating system 2 and a control system 3. The measurement operating system 2 has a table 4 on which a sample S, which is the object to be measured, is placed. The table 4 is driven by a table movement system 6 and is moved within a plane. The movement distance of the table 4 can be specified as the movement distance in the mutually orthogonal x- and y-directions.

The table movement system 6 can be composed of any parallel movement mechanism. For example, the mechanism can have a structure formed by causing a feed screw shaft to rotate by a motor capable of controlling the rotation angle, and connecting the table 4 to a mover threadably fitted to the feed screw. The motor capable of controlling the rotation angle is, for example, a servomotor, pulse motor, or the like.

A two-dimensional pixel camera 7 used as optical imaging means is provided on the periphery of the table 4. The two-dimensional pixel camera 7 is image pickup equipment formed by arranging a plurality of very small semiconductor photodetectors (hereinafter referred to as "pixels") in a planar manner. The camera 7 is driven by a camera readout drive system 8 for controlling the readout operation of the pixels, and outputs an output signal from the individual pixels as a camera signal S1 from an output terminal 7a. The camera 7 itself is secured and disposed in a predetermined position.

An X-ray optical system that includes an X-ray source 11 and an X-ray detector 12 is provided facing the table 4. The X-ray source 11 is, for example, an X-ray focal point inside of a hot cathode-type X-ray generator. The X-ray detector 12 in the present embodiment is composed of a two-dimensional X-ray detector formed by a plurality of very small semiconductor elements (hereinafter referred to as "pixels") that is arranged in a planar manner and that receives X-rays and outputs electric signals. It is apparent that other zero-dimensional, one-dimensional, or two-dimensional x-ray detectors having well-known configurations can be used.

An X-ray R1 emitted from the X-ray source 11 is incident on a single point P within the surface of the sample S on the table 4. The coordinate position of the point P is expressed by (x, y). In a case in which the X-ray R1 is incident on the sample S at the point P, a diffraction X-ray R2 is generated from the point P of the sample S at a diffraction angle 2θ when the crystal lattice surface inside of the sample S and the incident X-ray satisfy the Bragg diffraction conditions, which are predetermined diffraction conditions. The X-ray detector 12 is disposed in a position at which the diffraction X-ray R2 generated in such a way can be detected. The X-ray detector 12 scans and moves in the 2θ direction as necessary. As comprehended from above, the x-ray source 11 and the X-ray detector 12 are disposed in mutually opposite areas with the normal line (i.e., the normal line of the lattice surface) N' of the crystal lattice surface as the boundary therebetween. Note that the angle which is defined by the normal line N of the sample surface and the normal line N' of the lattice surface is referred to as φ.

The X-ray source 11 and the x-ray detector 12 are driven by an optical system movement device 13, and can rotatably move about an X-ray incidence position P. The φ angle can be altered by rotatably moving the X-ray source 11 and the X-ray detector 12 at the same time. In addition, the diffraction ray capture angle 2θ of the x-ray detector 12 can be altered by rotatably moving the x-ray source 11 and the x-ray detector 12 in a relative manner. The optical system movement device 13 can be formed by a suitable rotation mechanism in which a motor, for example, a servomotor, pulse motor, or other motor capable of controlling the angle of rotation is used as the power source.

The above measurement operating system 2 is a single example, and it is apparent that the measurement operating system 2 can be composed of another operating system having a suitable configuration as necessary.

The control system 3 has a CPU (Central Processing Unit) 15, a memory 16, a display 17, and a keyboard 18 and a mouse 19 as input means in the present embodiment. The memory 16 is composed of internal memory that is constituted by RAM (Random Access Memory), ROM (Read Only Memory), and the like; and external memory that is constituted by a hard disc, and the like. Any input device besides the keyboard and mouse can be used for the input means.

Programs such as a stress measurement program 20, an analysis program 21, an image formation program 22, and the like are stored in the memory 16. In addition, a measurement data file 24, which is an area for saving measurement results data, and an analysis data file 25, which is an area for saving analysis results data, are secured in the memory 16. Each of the stress measurement program 20, the analysis program 21, and the image formation program 22 works together with the CPU 15 and acts as function implementation means for implementing a predetermined function.

The stress measurement program 20 is a program for calculating internal stresses $\sigma_x$, $\sigma_y$, $\sigma_z$ at the X-ray incidence position (i.e., the measurement position) P of the sample S, the internal shearing stress τ, the peak width (FWHM: full width half maximum) of an X-ray profile, the diffracted X-ray intensity, the degree of orientation of the sample S, and the like by operating the components of the measurement operating system 2 in a predetermined sequential order. The stresses $\sigma_x$, $\sigma_y$, $\sigma_z$ and the shearing stress τ are calculated by measuring the alteration in the interval "d" between the lattice surfaces inside of the sample S using the X-ray diffraction measurement.

The analysis program 21 is a program for performing a predetermined analysis on the basis of the measurement data obtained as measurement results and saved in the measurement data file 24. The analysis results data is saved in the analysis data file 25. The image formation program 22 is a program for forming image information so that data such as $\sigma_x$, $\sigma_y$, or the like can be displayed as an image on a screen of the display 17.

A process carried out by the X-ray stress measurement apparatus 1 having the aforementioned configuration will be described below.

An operator first places the sample S, which is the object to be measured, in a decided predetermined position on the table 4. The area for which the measurement of the sample is desired is then photographed by the camera 7. The camera signal S1 obtained by the photography is transmitted to the CPU 15, and is saved in a predetermined area in the memory 16 as necessary.

Figure 2:
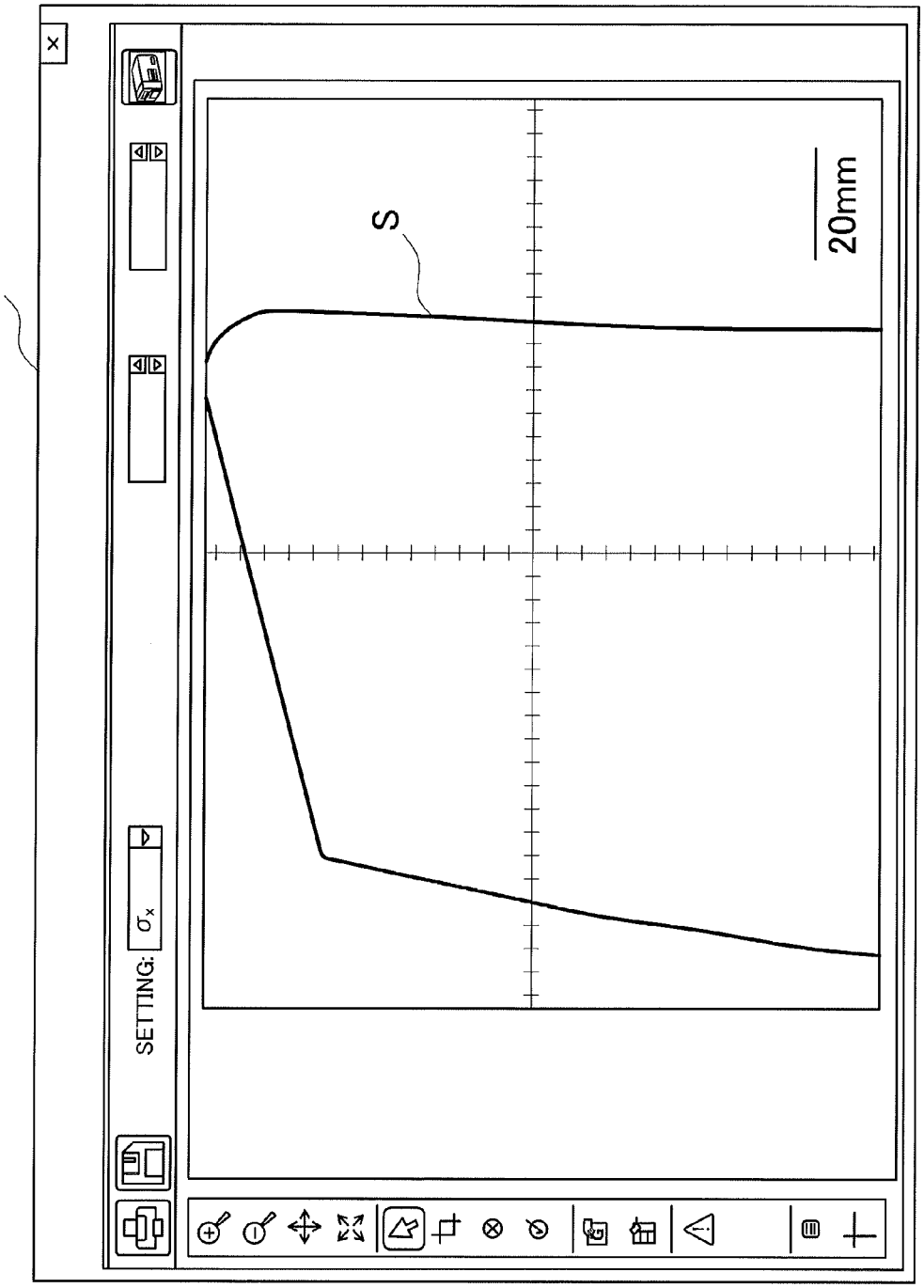
FIG. 2 is a view showing a state in which an optical image of a sample is displayed on a screen of a display.

The image formation program 22 forms image information that corresponds to the camera signal S1 at any timing. An image of the sample S is displayed on the screen of the display 17 by supplying the image information to the image display driver inside of the display 17. For example, an image of the sample S can be displayed on the screen of the display 17, as shown in FIG. 2.

First Example of a Mapping Display on an Optical Image

Figure 3:
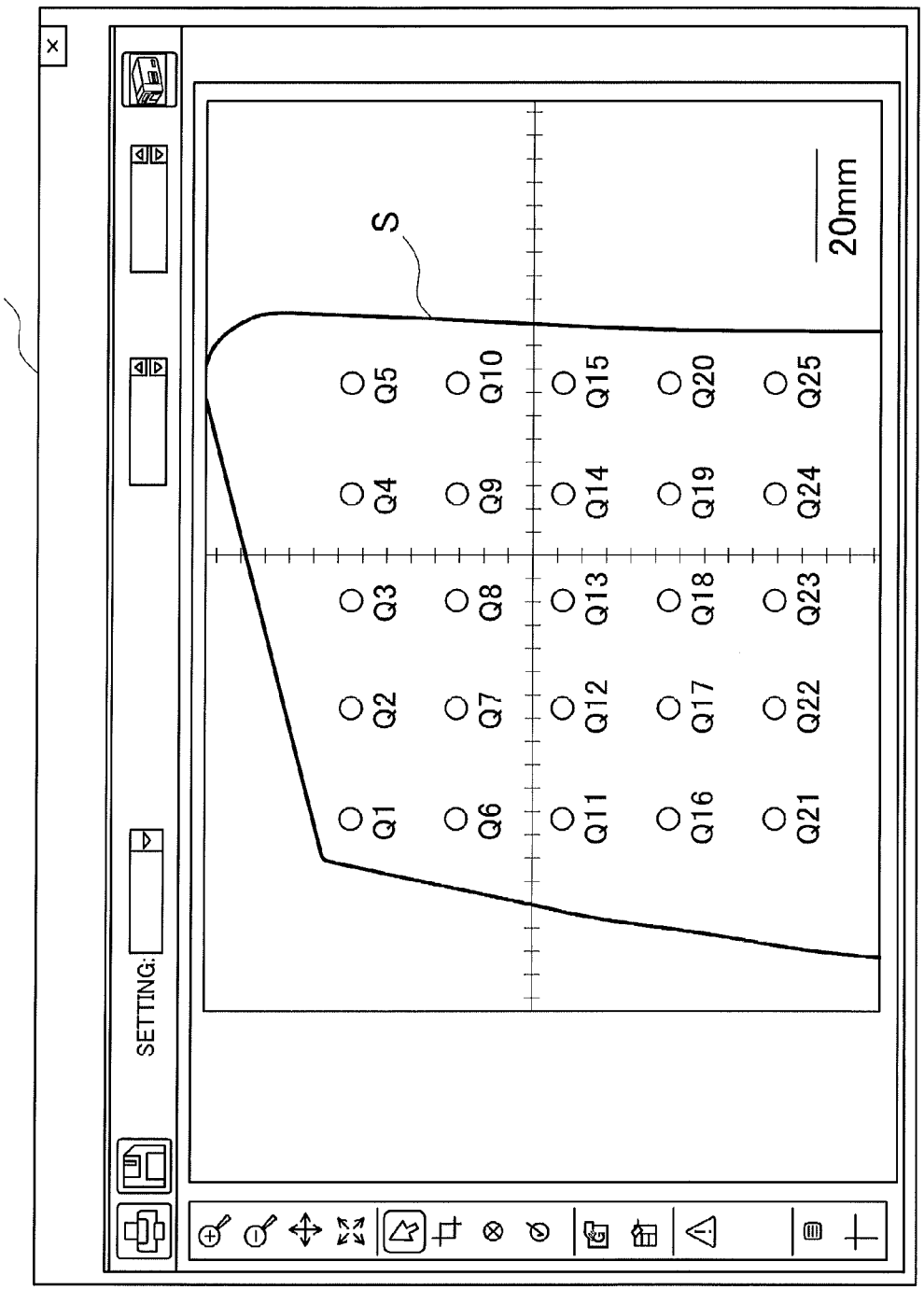
FIG. 3 is a view showing a state in which measurement positions of a sample are displayed on an optical image.

The stress measurement program 20 determines a plurality of measurement positions Q1, Q2, ..., Qn (n is an integer) in relation to the sample S in correspondence with an operation input by the operator, or in accordance with a procedure decided in advance. The measurement positions Q1, Q2, ..., Qn are displayed as, for example, 5×5=25 dots, as shown in FIG. 3. In this case, n=25.

The camera 7 used in the present embodiment is a camera in which the distance between each of the pixels of the optical image is evident in correspondence with optical magnification. The orientation and distance of the measurement positions coincide with the reference points of the device coordinates in terms of the pixels of the optical image. The measurement positions Q1, Q2, ..., Q25 decided in the manner described above are therefore matched one-to-one with the coordinate positions on the table 4 inside of the measurement operating system 2 of FIG. 1.

The stress measurement program 20 of FIG. 1 causes the table 4 to move, whereby the measurement positions Q1, Q2, ..., Q25 of the sample S of FIG. 1 that correspond to the measurement positions Q1, Q2, ..., Q25 decided in FIG. 3 are sequentially transported toward, namely shifted to, the X-ray incidence position P. Stress measurement using the X-ray is then sequentially carried out at the individual measurement positions Q1, Q2, ..., Q25. During measurement, an output signal S2 of the X-ray detector 12 is transmitted to the CPU 15. The CPU 15 carries out computation following the process defined by the stress measurement program 20, and calculates the material properties information (i.e., the physical quantities) relating to the sample S, such as the internal stresses $\sigma_x$, $\sigma_y$, $\sigma_z$, the internal shearing stress $\tau$, the peak width (FWHM: full width half maximum) of the X-ray profile, the diffraction X-ray strength, the degree of orientation of the sample S, and the like for the individual measurement positions Q1, Q2, ..., Q25. The calculated material properties information is saved in the measurement data file 24 in a state in which each is linked to the corresponding measurement positions Q1, Q2, ..., Q25.

After the measurement data is thus calculated, the image formation program 22 of FIG. 1 maps and displays the calculated material properties information in terms of an optical image in a manner described below. A mapping display refers to displaying material properties information such as stress or the like in association with the measurement positions Q1, Q2, ..., Q25 of the sample.

Figure 4:
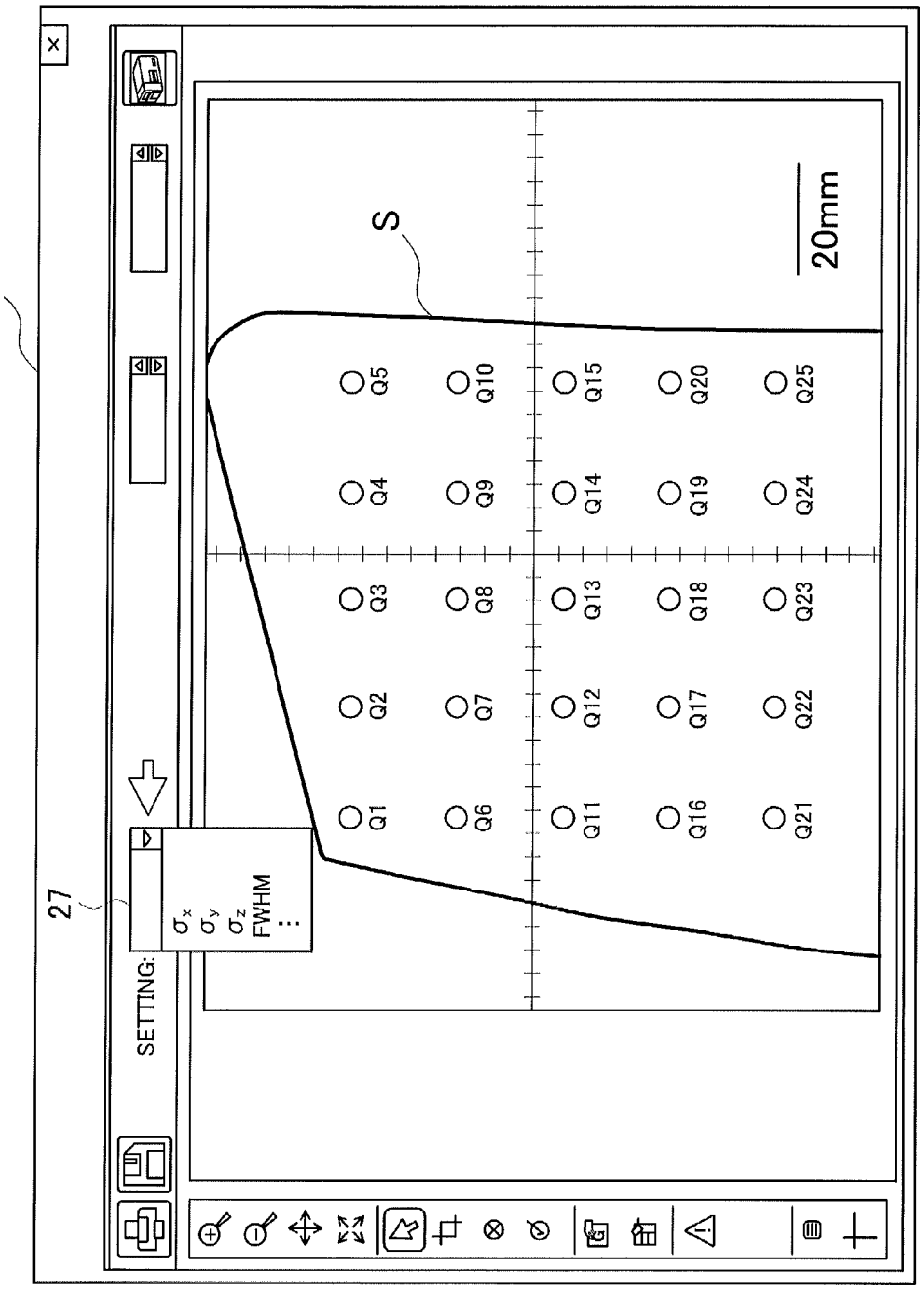
FIG. 4 is a view showing a screen display when material properties information, which is a physical quantity, is selected.

In FIG. 4, the operator first aligns the mouse pointer with a selection column 27 of the material properties information, and clicks the mouse. The selectable material properties information is then displayed inside of a pull-down menu. The drawing shows an example of a case in which the stress $\sigma_x$ in the x-direction, the stress $\sigma_y$ in the y-direction, the stress $\sigma_z$ in the z-direction, and the FWHM are displayed as the selectable material properties information.

Figure 5:
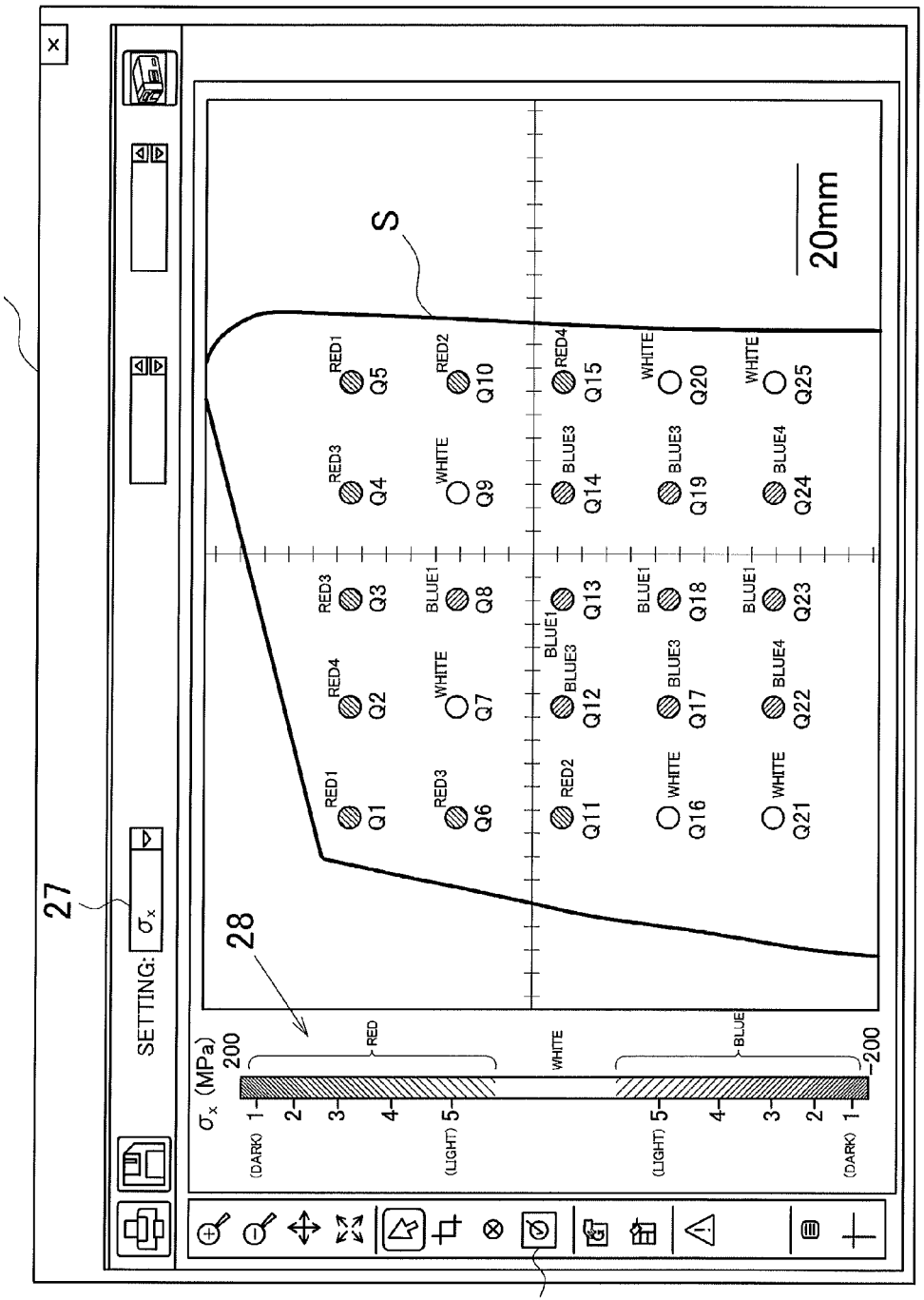
FIG. 5 is a view showing an embodiment of a mapping display that is displayed on a screen of a display.

The operator selects, for example, $\sigma_x$, and "$\sigma_x$" is displayed in the selection column 27, as shown in FIG. 5. This is the display of the stress direction. A mapping display is then performed by a gradient shading display of three colors, red, white, and blue. Specifically, a shading scale 28 of three colors, red, white, and blue, is displayed on the left part of the window display. In the shading scale 28, the intermediate part is a white color, the part above the white color is a red color, and the part below the white color is a blue color.

The red color has a dark density on the upper part, and the density becomes lighter approaching the white color of the intermediate part. The alteration in density is actually absent of levels, but divisions are attached to the locations of reference numerals 1, 2, 3, 4, and 5 in the drawing in order to make the description easier to understand. When viewed in terms of high and low density, red 1 is greater than red 2, which is greater than red 3, which is greater than red 4, which is greater than red 5.

In the same manner, the blue color has a dark density on the lower part, and becomes lighter approaching the white color of the intermediate part. The alteration in density is actually absent of levels, but divisions are attached to the locations of reference numerals 1, 2, 3, 4, and 5 in the drawing in order to make the description easier to understand. When viewed in terms of high and low density, blue 1 is greater than blue 2, which is greater than blue 3, which is greater than blue 4, which is greater than blue 5.

The red color expresses that the stress is "positive" (i.e., tensile stress). The maximum endpoint of the red color expresses that $\sigma_x$=200 MPa. The white color expresses that $\sigma_x$=0 MPa. The blue color expresses that the stress is "negative" (i.e., compressive stress). The minimum endpoint of the blue color expresses that $\sigma_x$=−200 MPa.

In the mapping display of FIG. 5, the size (diameter) of the circular marks of the measurement positions Q1, Q2, ..., Q24, Q25 are all the same. The color display of the measurement positions Q1, Q2, ..., Q24, Q25 is as shown in the following table.

TABLE 1

| Position | Color (Density) |
| --- | --- |
| Q1 | RED1 |
| Q2 | RED4 |
| Q3 | RED3 |
| Q4 | RED3 |
| Q5 | RED1 |
| Q6 | RED3 |
| Q7 | WHITE |
| Q8 | BLUE1 |
| Q9 | WHITE |
| Q10 | RED2 |
| Q11 | RED2 |
| Q12 | BLUE3 |
| Q13 | BLUE1 |
| Q14 | BLUE3 |
| Q15 | RED4 |
| Q16 | WHITE |
| Q17 | BLUE3 |
| Q18 | BLUE1 |
| Q19 | BLUE3 |
| Q20 | WHITE |
| Q21 | WHITE |
| Q22 | BLUE4 |
| Q23 | BLUE1 |
| Q24 | BLUE4 |
| Q25 | WHITE |

Figure 6:
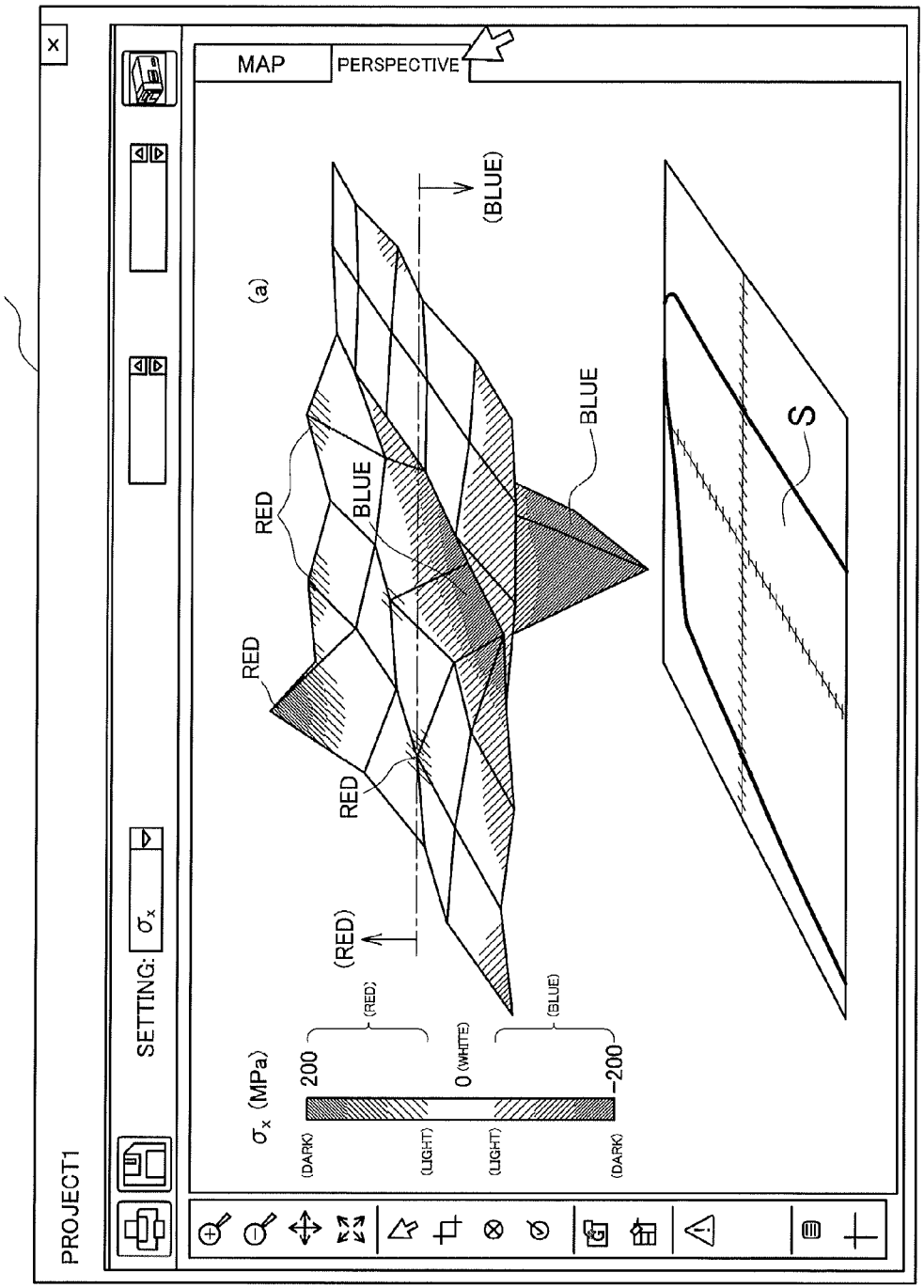
FIG. 6 is a view showing a state in which the mapping display shown in FIG. 5 is displayed on the display as a three-dimensional stress distribution diagram.

By viewing the mapping display of FIG. 5, the operator can immediately judge that the stress $\sigma_x$ of the sample S in the x-direction is as shown three-dimensionally in FIG. 6(A). That is, the operator can readily, intuitively, and accurately become aware of $\sigma_x$, i.e., the material properties information, for each part Q1, Q2, . . . , Q24, Q25 of the sample S.

Thumbnail Display

The image formation program 22 of FIG. 1 can perform a thumbnail display of $\sigma_x$ of the measurement position for each of the individual measurement positions Q1, Q2, . . . , Q24, Q25 of FIG. 5. A thumbnail display is a display in which the image desired to be displayed is reduced in size and concisely compiled, and is a display for allowing a summary of the contents of the image desired to be displayed to be readily comprehended at a glance.

Figure 7:
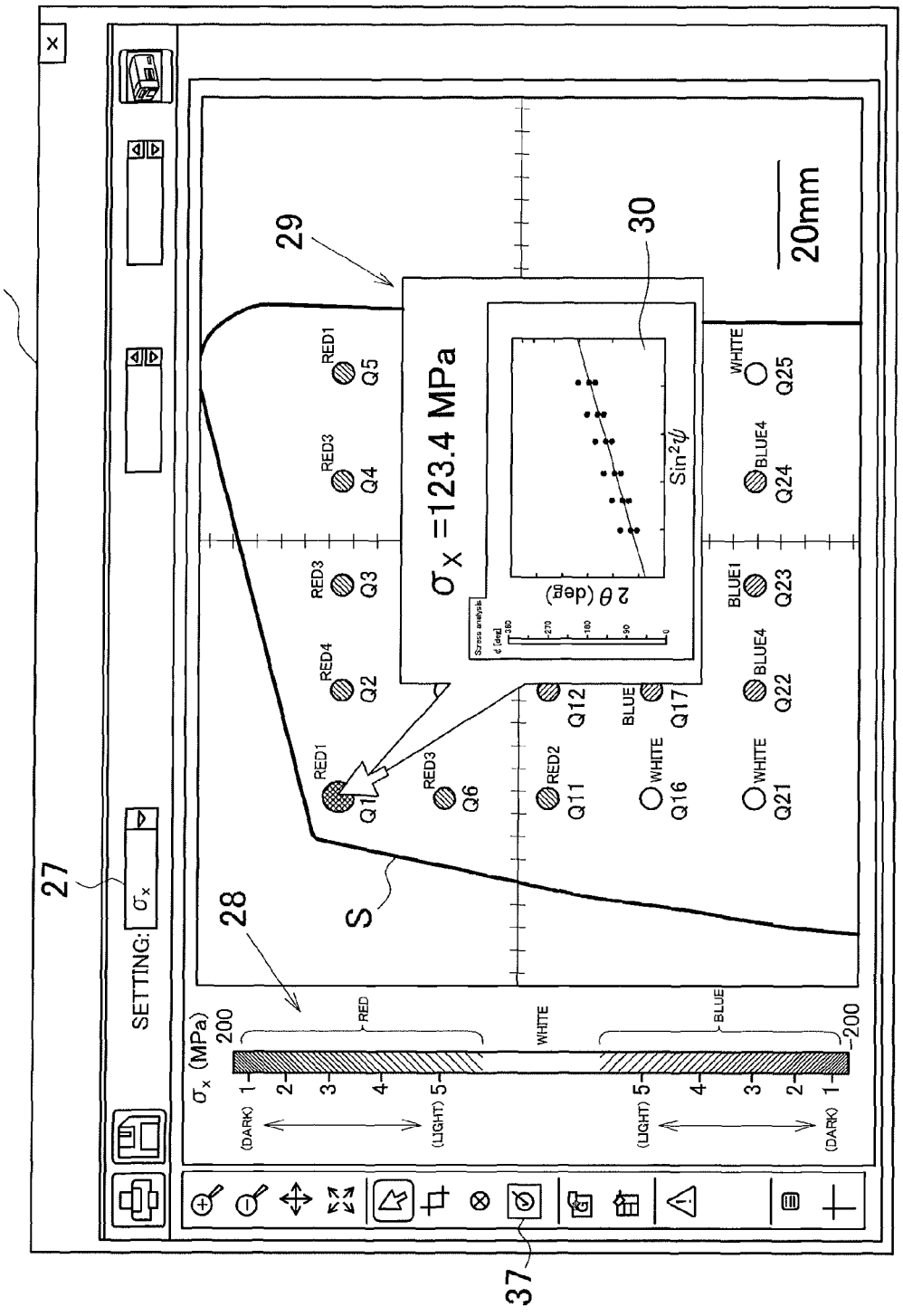
FIG. 7 is a view showing a thumbnail display performed in association with the mapping display of FIG. 5.

In the present embodiment, a thumbnail display 29 is displayed when a measurement position desired to be displayed as a thumbnail (for example, measurement position Q1 of FIG. 7) is clicked once by the mouse. A $2\theta$-$\sin^2 \phi$ diagram 30 is included in the thumbnail display 29 as an example. The operator who views this thumbnail display can become aware that $\sigma_x$ is calculated using the $2\theta$-$\sin^2 \phi$ diagram.

Startup of Analytical Software

Figure 8:
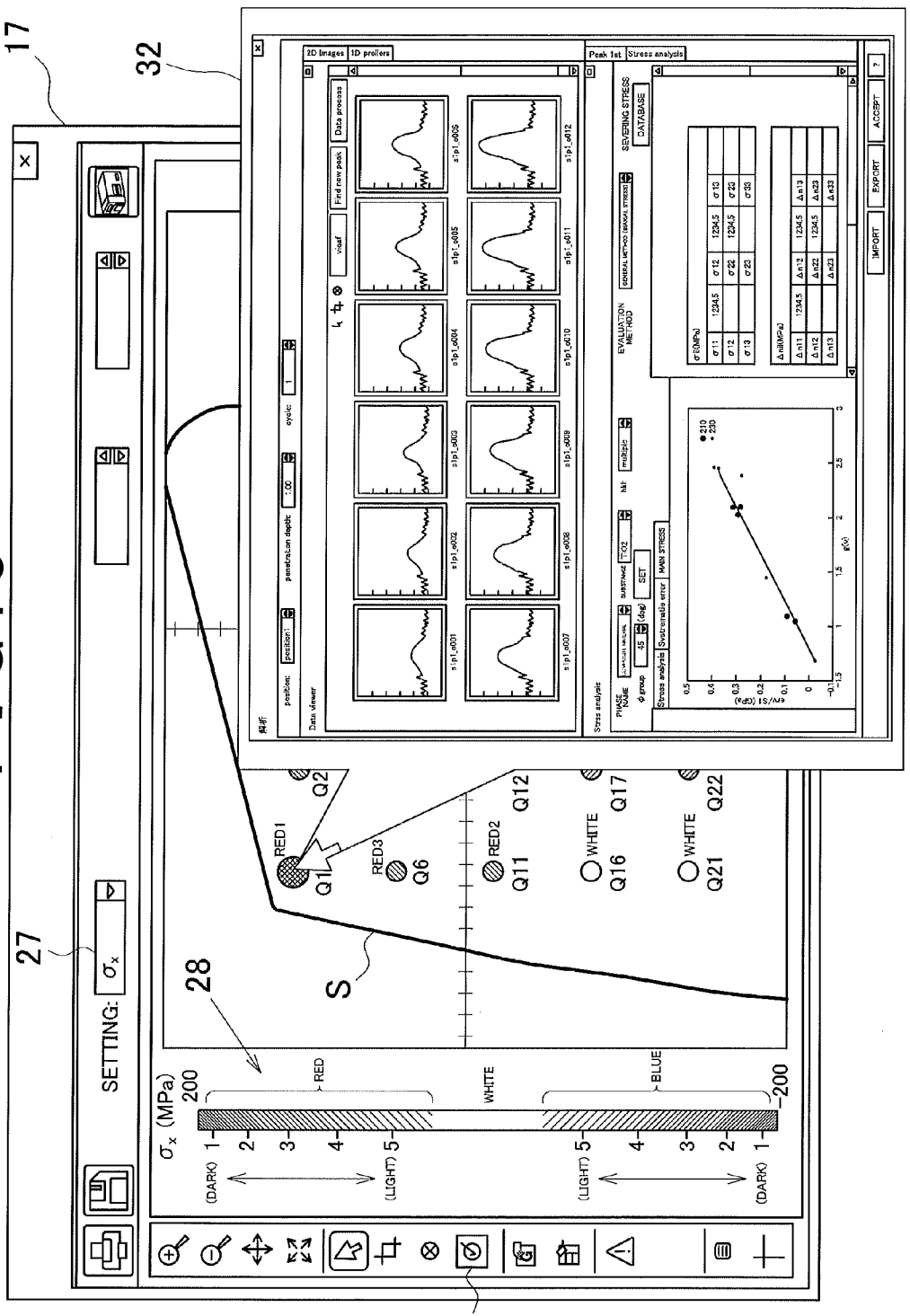
FIG. 8 is a view showing a screen display of the analysis process performed in association with the mapping display of FIG. 5.

In addition, in a case in which analysis is desired, the operator double clicks the desired measurement position using the mouse. The analysis program 21 of FIG. 1 is then started, an analysis dialogue window 32 is displayed, and analysis can be performed by the operator, as shown in FIG. 8. The operator can perform analysis using the analysis dialogue window 32. Analysis results are saved in the analysis data file 25 of FIG. 1.

Visualization of Distinctive Points

In measurements using the X-ray stress measurement apparatus 1 according to the present embodiment, it is thought that the operator in many cases wants to know whether the measurement points Q1, Q2, . . . , Q24, Q25 of the sample S are distinctive points. Here, a distinctive point refers to a small area inside of the sample S when the small area is in a state outside of a range of permissible values relative to predetermined parameters. In a case in which a distinctive point is present inside of the sample S, the sample S is usually judged to be unsuitable for use.

The parameters are suitably selected in accordance with the requirements of the operator. Generally, a plurality of parameters is set. In the present embodiment, four physical quantities are decided as parameters: the stress $\sigma_x$ in the x-direction, the stress $\sigma_y$ in the y-direction, the stress $\sigma_z$ in the z-direction, and the peak width of the diffraction X-ray (FWHM: full width half maximum). The predetermined permissible range values are set in advance by the operator or are set as the default values of the program in relation to the physical quantities.

For example, a distinctive point is a case in which the value exceeds 150 MPa in relation to $\sigma_x$ and $\sigma_y$. In addition, a distinctive point is a case in which the value is lower than −150 MPa or exceeds 150 MPa in relation to $\sigma_z$. Furthermore, a distinctive point is a case in which the value exceeds 7.50° in relation to the peak full width half maximum.

Figure 9:
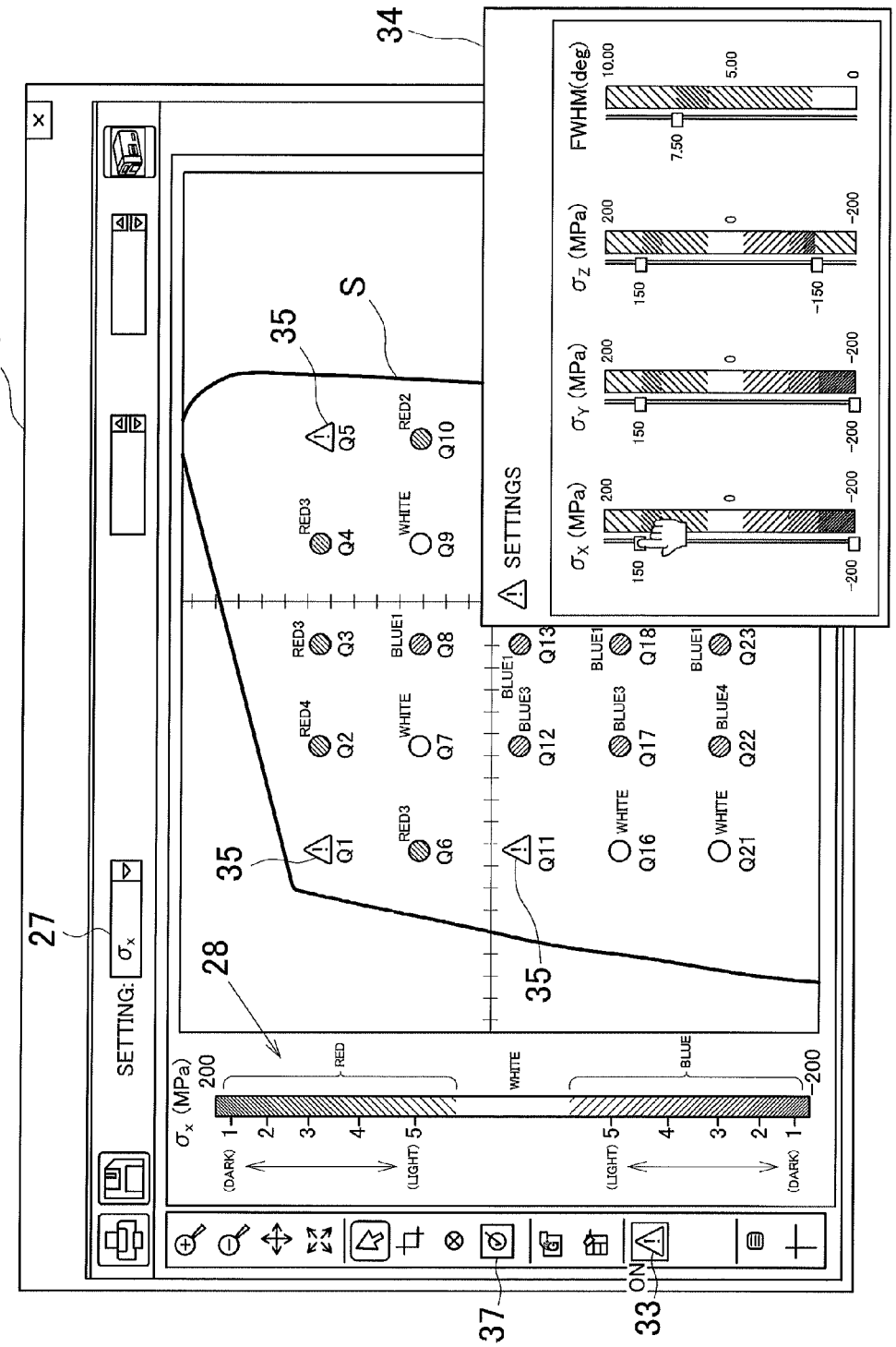
FIG. 9 is a view showing a screen display during the visualization process of the distinctive points performed in association with the mapping display of FIG. 5.

In the present embodiment, a settings button 33 for distinctive points is clicked by the operator in FIG. 9, whereupon the stress measurement program 20 of FIG. 1 enters "Visualization of Distinctive Point" Mode. A settings dialogue window 34 of FIG. 9 is then displayed. Parameters $\sigma_x$, $\sigma_y$, $\sigma_z$, and FWHM are displayed in the settings dialogue window 34, and the permissible range values of the parameters are also displayed. A warning display 35 is displayed at the location of the measurement position when the parameters of at least one of the measurement positions Q1, Q2, . . . , Q24, Q25 is outside of the permissible range values. By viewing the warning display 35, the operator can readily recognize in which portion of the sample S a distinctive point is.

Feedback Measurement

The operator viewing the mapping display of FIG. 5 can readily and accurately conclude how the internal stress of the sample S is distributed. In this case, the operator sometimes desires to know what the stress state is in portions other than the measurement positions Q1, Q2, . . . , Q24, Q25.

Figure 10:
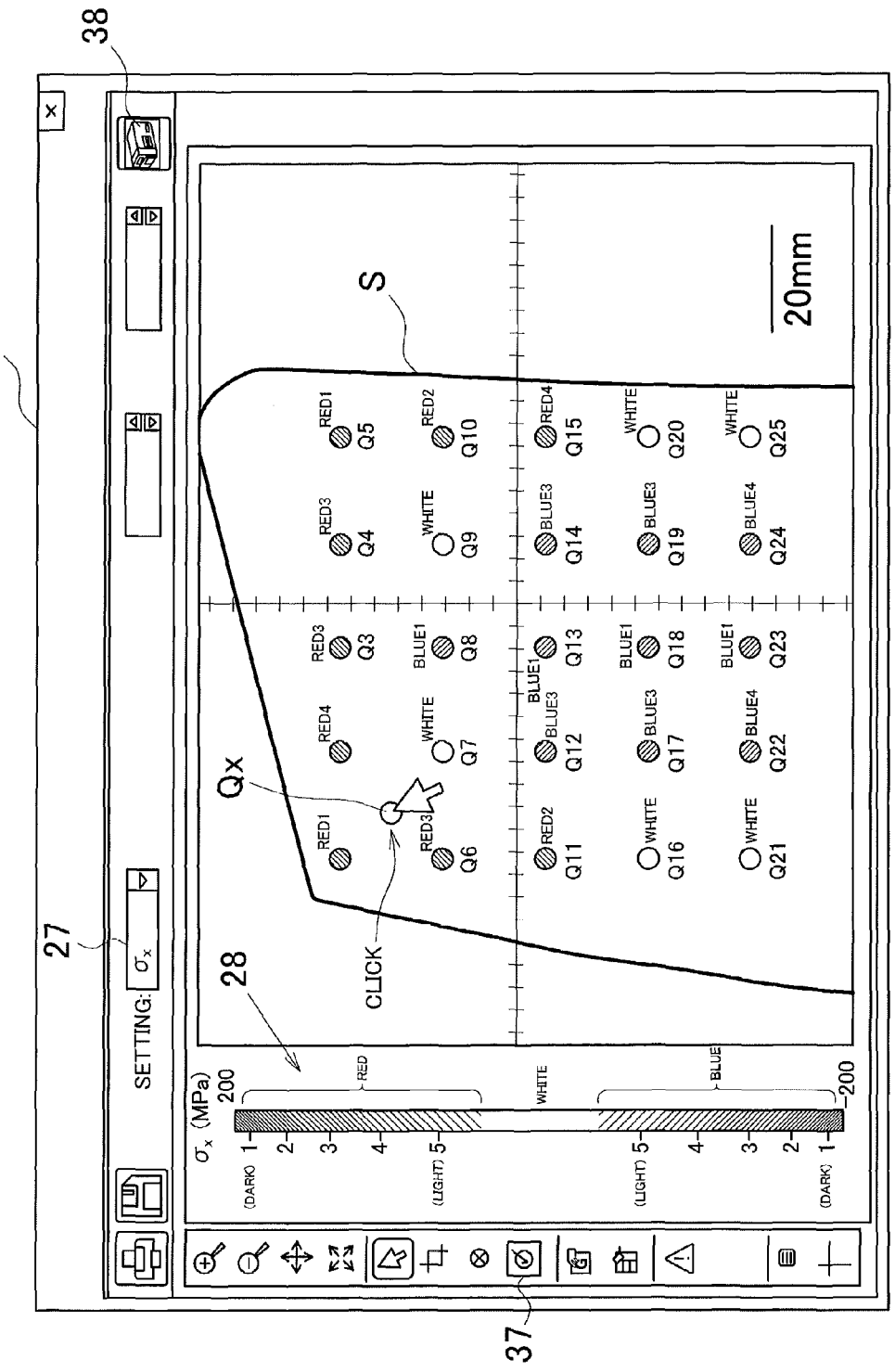
FIG. 10 is a view showing a screen display during the feedback measurement process performed in association with the mapping display of FIG. 5.
Figure 11:
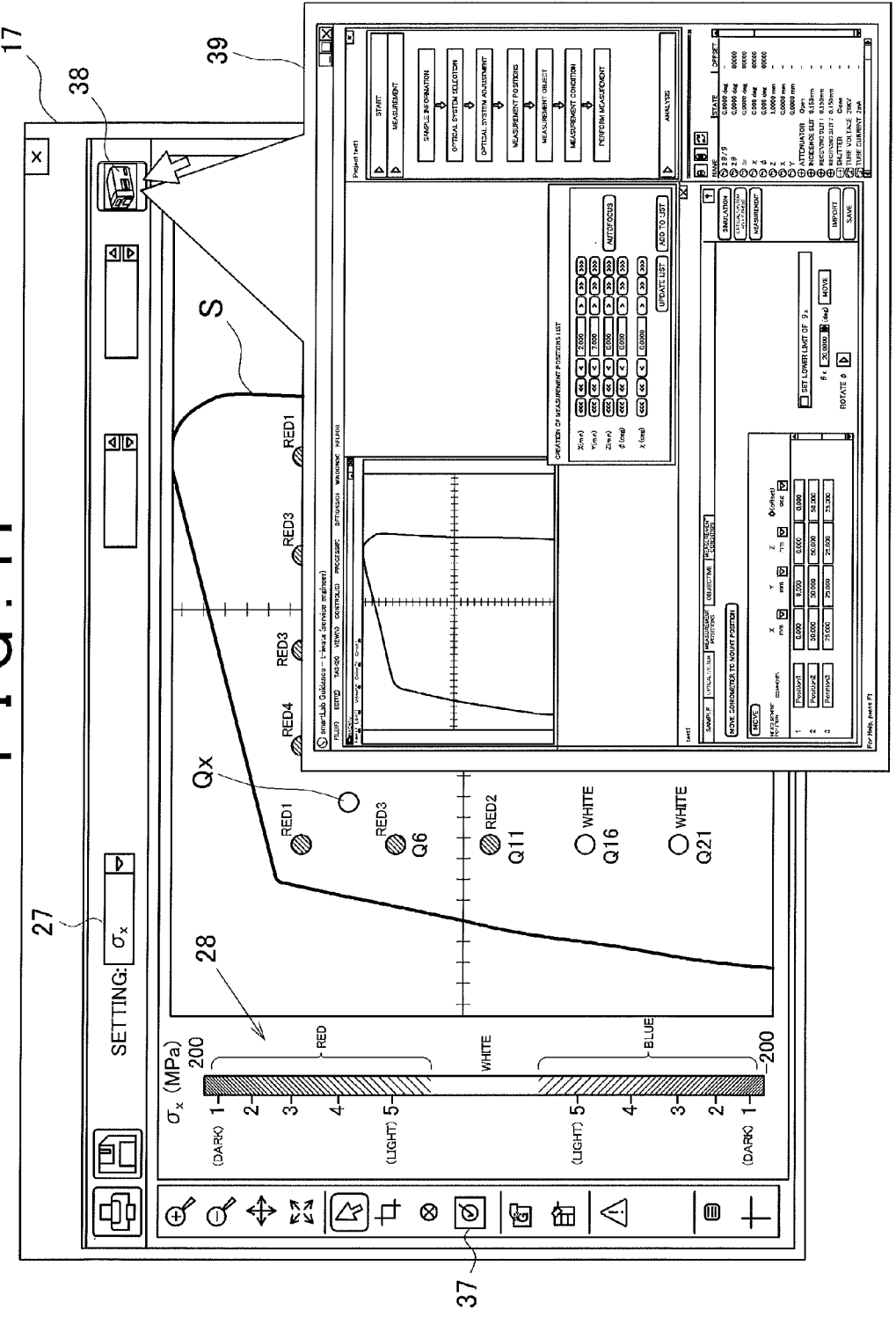
FIG. 11 is a view showing a screen display displayed in succession with the display of FIG. 10.

In this case, the operator aligns the pointer with an additional measurement point button 37 of FIG. 5, and clicks the mouse. The stress measurement program 20 of FIG. 1 then enters Additional Measurement Mode. After the Additional Measurement Mode is started, the operator indicates a desired measurement position $Q_x$ by clicking, as shown in FIG. 10, and stress measurement is again carried out by the stress measurement program 20 when a measurement button 38 on the upper right is clicked. At this time, a measurement dialogue window 39 is displayed on the screen of the display 17, as shown in FIG. 11.

Figure 12:
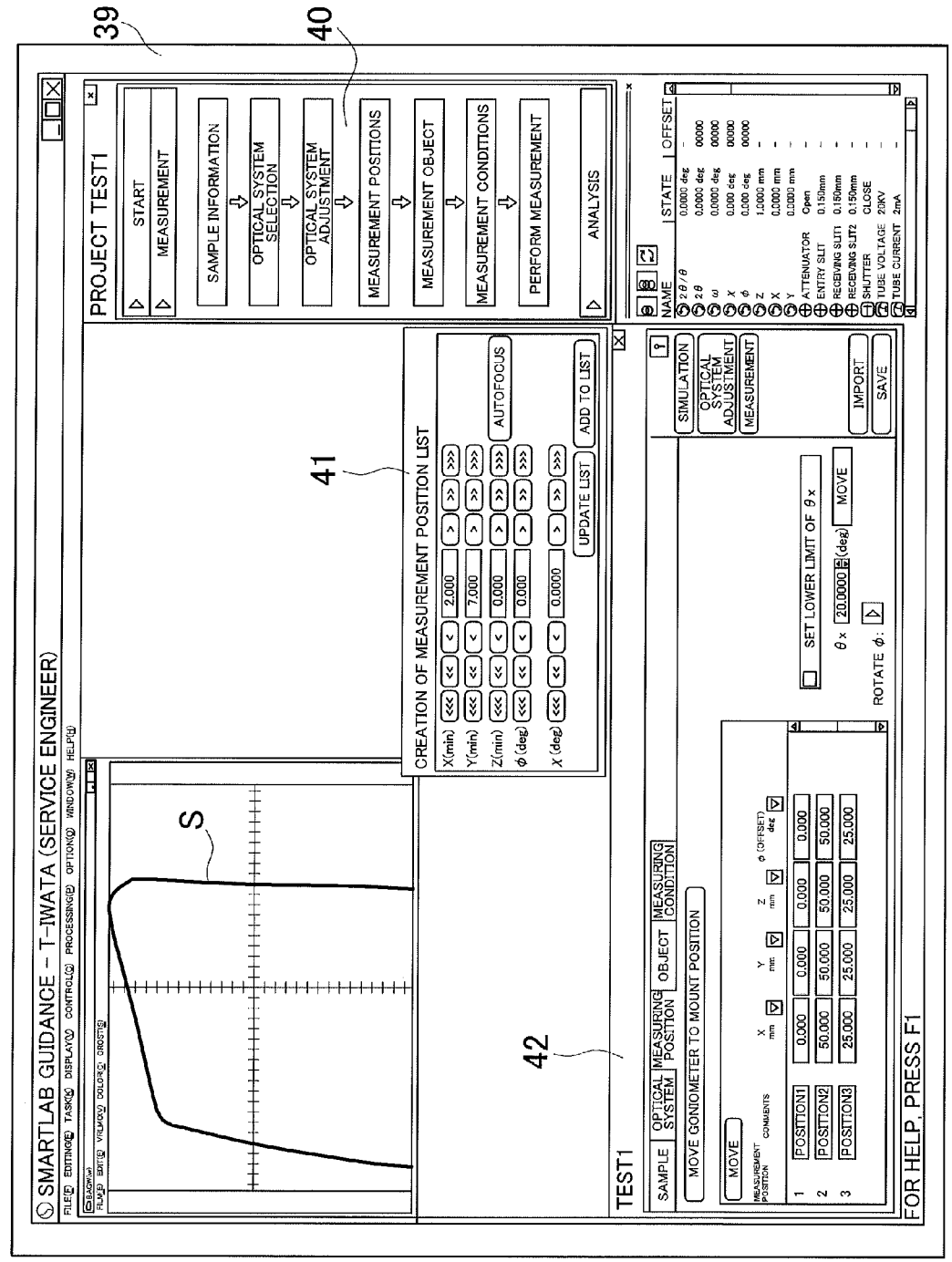
FIG. 12 is an enlarged view of the main part of FIG. 11.

The details of the measurement dialogue window 39 are enlarged and are as shown in FIG. 12. In FIG. 12, a flow bar 40 displays the type of flow used when a measurement is performed, as well as the current stage of measurement. A window 41 for creating a measurement list is used as an input window when the operator controls the position of the table. A measurement position window 42 expresses the next measurement points to be measured. In the drawing, the measurement position window expresses the next three measurement points to be measured. The window displays 40, 41, 42 are set to the display state, closed on the screen, or otherwise manipulated in accordance with the desire of the operator.

Second Example of a Mapping Display on an Optical Image

In the first mapping display example shown in FIG. 5, the size of the circular dots expressing the positions of the measurement positions Q1, Q2, . . . , Q24, Q25 was the same size at every position. "Positive" stress was expressed by a red color, "negative" stress was expressed by a blue color, and the absolute value of the stress was displayed by the difference in shade of red color or blue color.

Figure 13:
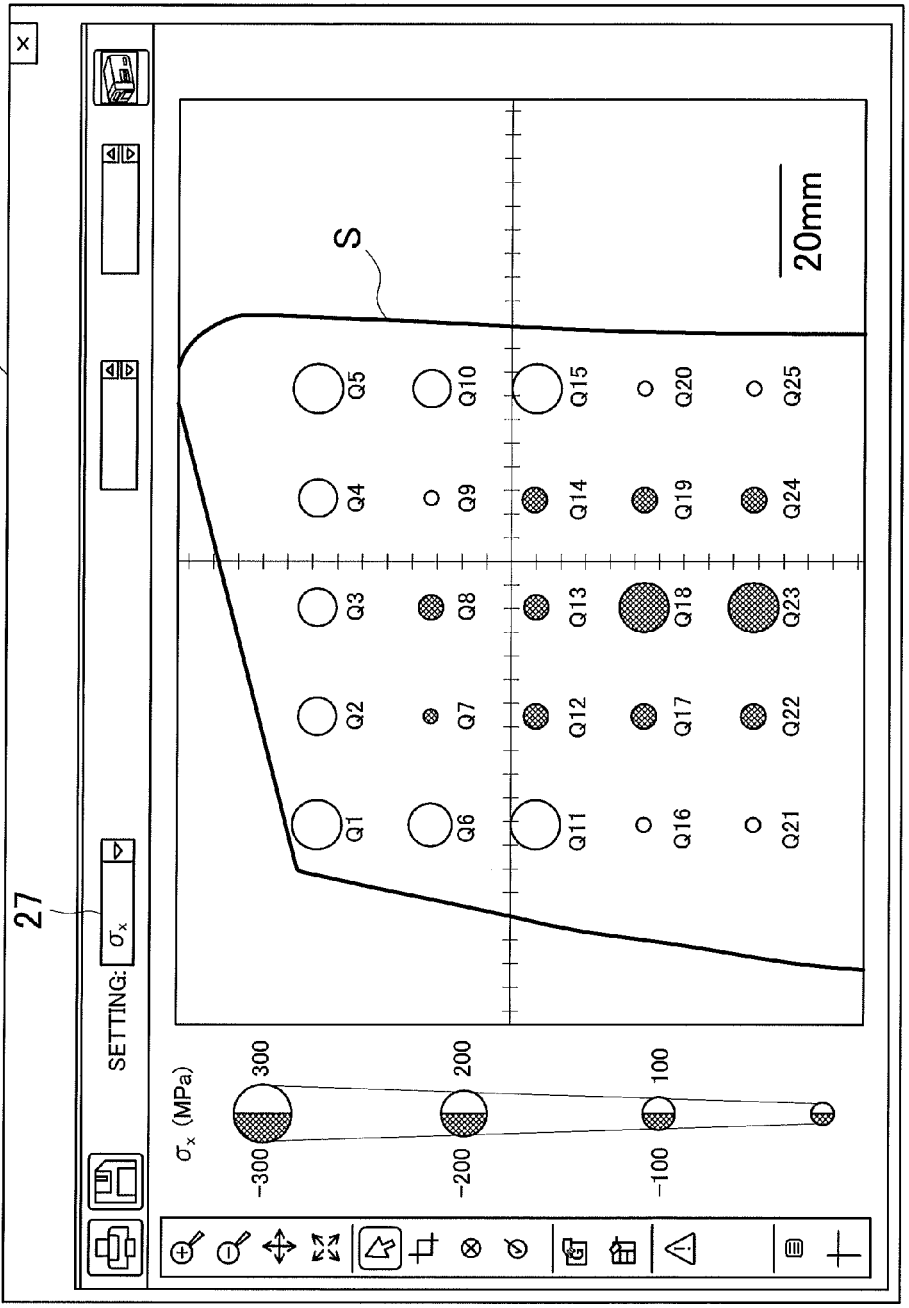
FIG. 13 is a view showing another embodiment of a mapping display displayed on the screen of a display.

In contrast, in the present embodiment shown in FIG. 13, positive and negative stresses are represented by whether the circular dot representing the measurement position is an empty ring or a filled circle rather than by the difference in color, and the absolute value of the stress is expressed by the size of the circular dot. The color of the circular dot is any single color. In the present embodiment as well, "$\sigma_x$" in the selection column 27 expresses the direction of the stress.

Even in a case in which a mapping display of the present embodiment is performed, it is apparent that the aforedescribed "thumbnail display," "startup of analytical software," "visualization of distinctive points," and "feedback measurement" can be performed.

Third Example of a Mapping Display on an Optical Image

Figure 14:
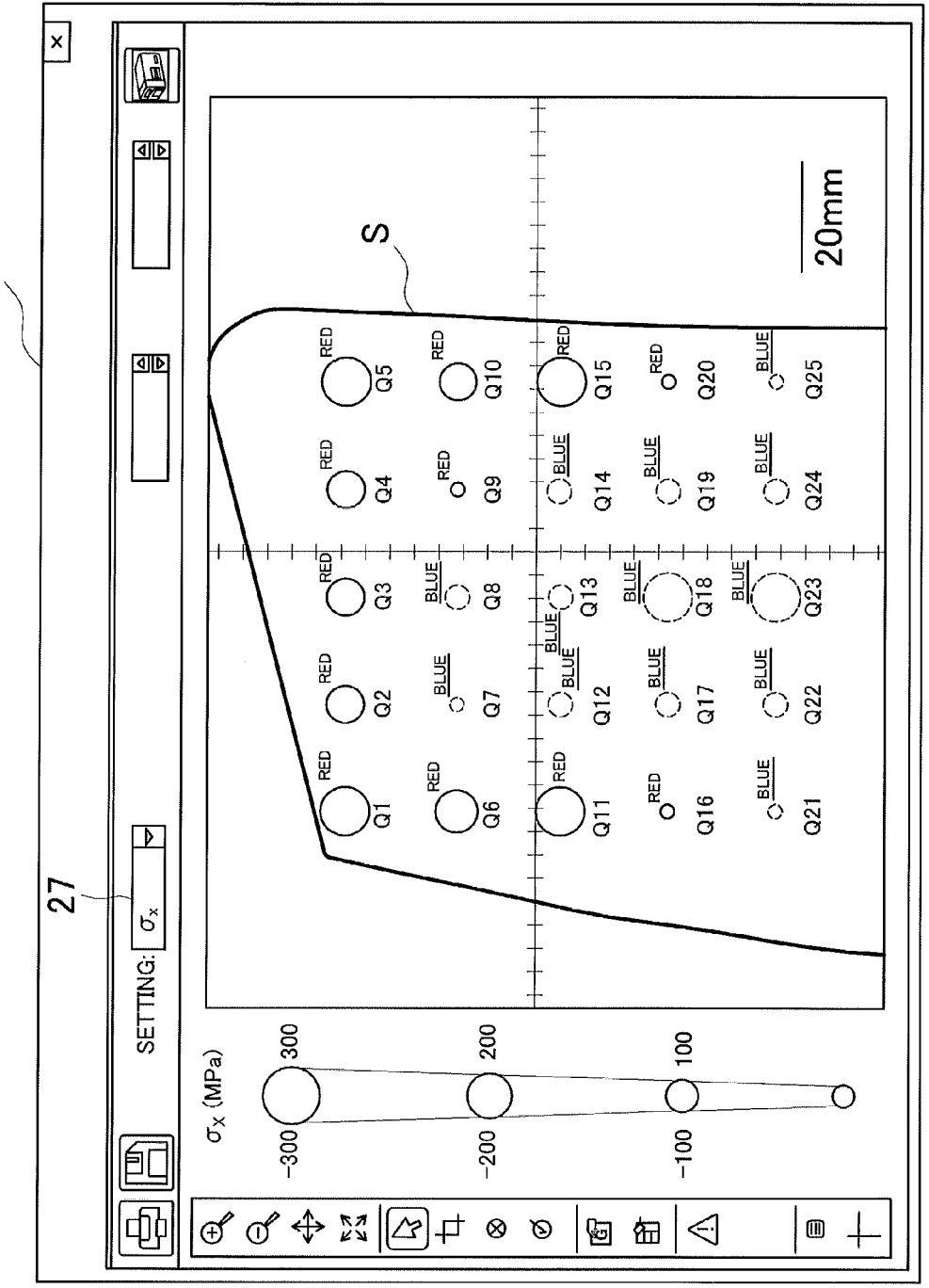
FIG. 14 is a view showing yet another embodiment of a mapping display displayed on the screen of a display.

In the second mapping display example shown in FIG. 13, positive and negative stresses were represented by leaving the ring of a single-color dot empty, or filling in the ring, and the absolute value of the stress was represented by the size of the dot. In contrast, in the present embodiment, the dots expressing the measurement positions Q1 to Q25 are all circular rings, positive and negative stress is expressed by a change in color, for example, "positive" is "red," and "negative" is "blue," and the absolute value of the stress is expressed by the size (diameter) of the ring, as shown in FIG. 14. In the present embodiment as well, "$\sigma_x$" in the selection column 27 expresses the direction of the stress.

Even in a case in which a mapping display of the present embodiment is performed, it is apparent that the aforedescribed "thumbnail display," "startup of analytical software," "visualization of distinctive points," and "feedback measurement" can be performed.

Fourth Example of a Mapping Display on an Optical Image

Figure 15:
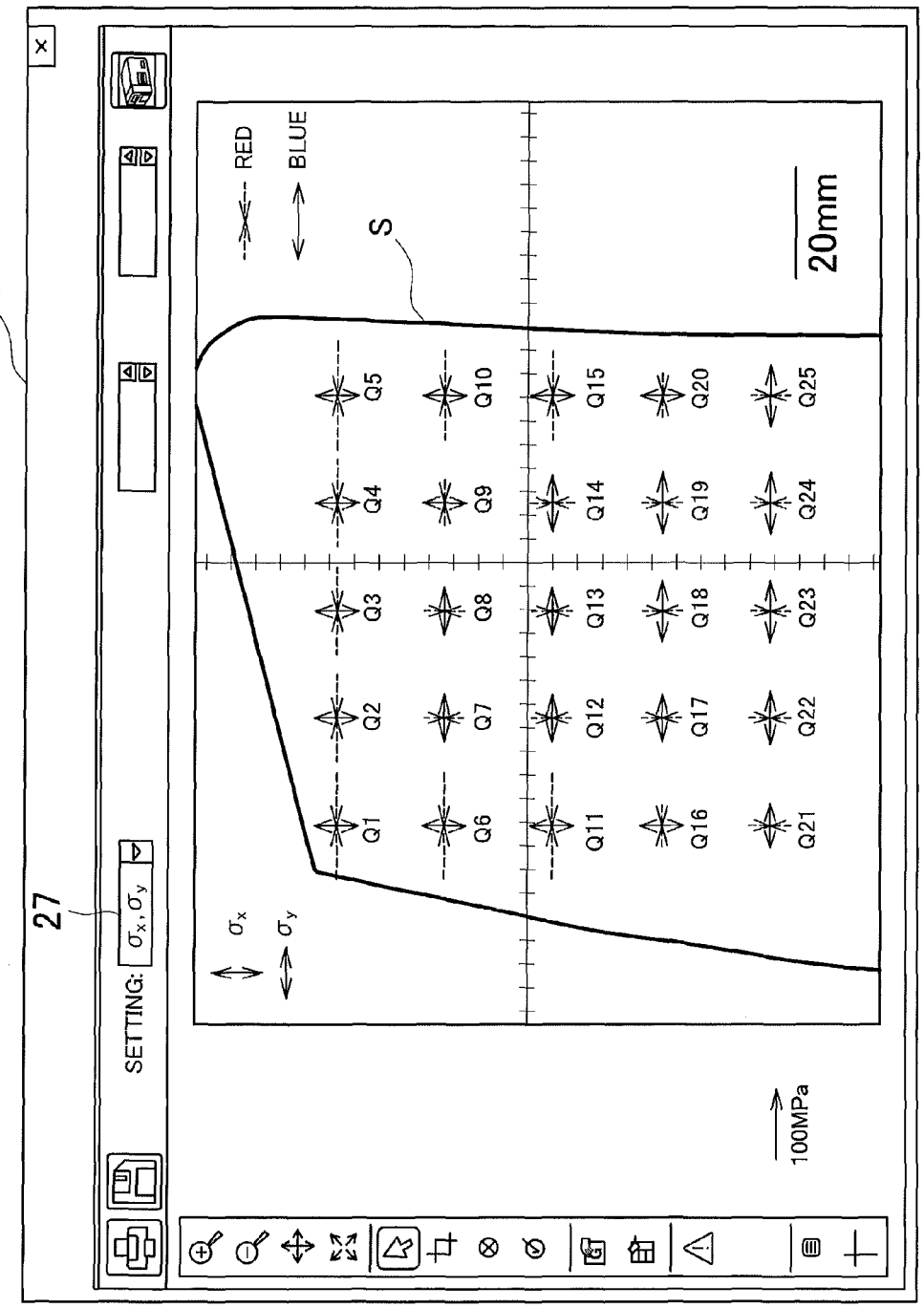
FIG. 15 is a view showing yet another embodiment of a mapping display displayed on the screen of a display.

In the first example shown in FIG. 5, the second example shown in FIG. 13, and the third example shown in FIG. 14, $\sigma_x$, which is a single physical quantity, is displayed on a single screen. In contrast, in the present embodiment, $\sigma_x$ and $\sigma_y$, which are two physical quantities, are displayed at the same time on a single screen, as shown in FIG. 15. Specifically, two different stress directions are displayed on a screen at the same time.

Specifically, $\sigma_x$ is displayed by a vertical arrow, and $\sigma_y$ is expressed by a horizontal arrow that is orthogonal to the vertical arrow. In addition, measurement points Q1, Q2, . . . , Q24, Q25 are expressed by the intersection of the arrows. In addition, compressive stress is expressed by arrows facing each other, and tensile stress is expressed by arrows pointing away from each other. Furthermore, the magnitude of the stress is represented by the length of the arrows. The arrows facing each other (compressive stress) are displayed in "red," and the arrows pointing away from each other (tensile stress) are displayed in "blue," whereby stress can be intuitively and accurately recognized.

According to the present embodiment, two physical quantities, $\sigma_x$ and $\sigma_y$, can be observed on a single screen, which is therefore very advantageous in that analysis can be performed in a short period of time. It is particularly important in stress measurement that the stress in the x-direction and the stress in the y-direction be observed, but the present embodiment is very convenient in that both can be observed at the same time.

Even in a case in which a mapping display of the present embodiment is performed, it is apparent that the aforedescribed "thumbnail display," "startup of analytical software," "visualization of distinctive points," and "feedback measurement" can be performed.

Other Embodiments

Preferred embodiments of the present invention were described above, but the present invention is not limited to these embodiments, and can be variously modified within the scope of the invention described in the claims.

For example, a plate-shaped sample was given as an example in the above embodiments, but any shape may be used for the sample. In addition, a single kind of stress measurement method that uses an X-ray was given as an example in FIG. 1, but the measurement method is not limited to the example in the drawing. In addition, twenty-five points, Q1 to Q25, were used as measurement points in the above embodiments, but any number of measurement points may be used.

DESCRIPTION OF REFERENCE SYMBOLS

1. X-ray stress measurement apparatus, 2. Measurement operating system, 3. Control system, 4. Table (sample conveyance means), 6. Table movement system, 7. two-dimensional pixel camera (optical imaging means), 7a. output terminal, 8. camera readout drive system, 11. X-ray source, 12. X-ray detector, 13. optical system movement device, 15. CPU, 16. memory, 17. display, 18. keyboard (input means), 19. mouse (input means), 20. stress measurement program, 21. analysis program, 22. image formation program, 24. measurement data file, 25. analysis data file, 27. selection column (direction notation symbols), 28. shading scale, 29. thumbnail display, 30. $2\theta$-$\sin^2 \phi$ diagram, 32. analysis dialogue window, 33. settings button, 34. settings dialogue window, 35. warning display, 37. additional measurement point button, 38. measurement button, 39. measurement dialogue window, 40. flow bar, 41. window for creating a measurement list, 42. Measurement position window, N. Normal line of sample, N'. Normal line of lattice surface, P. X-ray incidence point (measurement point), Q1-Q25. Measurement positions, Qx. Additional measurement position, R1. X-ray, R2. Diffraction X-ray, S. Sample, S1. Camera signal, S2. Output signal, $2\theta$. Diffraction angle, $\phi$. $\phi$ angle

What is claimed is:

1. An X-ray stress measurement apparatus comprising: optical imaging means for picking up an optical image of a sample;
  a display for displaying the optical image of the sample;
  input means capable of inputting positions on a screen of the display;
  an X-ray source for generating an X-ray;
  sample transporting means for moving the sample;
  X-ray detection means for detecting the X-ray exiting from the sample;
  measurement means for controlling the operation of the optical imaging means, the display, the input means, the X-ray source, the sample transporting means, and the X-ray detection means, determining measurement positions of the sample on the basis of the positions indicated by the input means, and measuring the determined measurement positions of the sample;
  stress computation means for computing the stress at the measurement positions of the sample on the basis of an output signal from the X-ray detection means; and
  image formation means for causing the optical image of the sample, the measurement positions of the sample, the absolute value of the stress, and the direction of the stress to be displayed on the same screen of the display.

2. The X-ray stress measurement apparatus according to claim 1, wherein the image formation means:
  displays the measurement positions of the sample by dots;
  displays the absolute value of the stress by shades of color of the dots;
  displays positive and negative stress using a classification of the color of the dots; and
  displays the direction of application of the stress using direction notation symbols.

3. The X-ray stress measurement apparatus according to claim 2, wherein the measurement means performs measurement in relation to the measurement positions of the sample when the measurement positions of the sample are indicated by the input means in a state in which the optical image of the sample, the measurement positions of the sample, the absolute value of the stress, the positive and negative stress, and the direction of application of the stress are visually displayed on the display.

4. The X-ray stress measurement apparatus according to claim 1, wherein the image formation means:
  displays the measurement positions of the sample by dots;
  displays the absolute value of the stress by the size of the dots;
  displays positive and negative stress using a pattern in which the dots are empty or a pattern in which the dots are filled; and
  displays the direction of application of the stress using direction notation symbols.

5. The X-ray stress measurement apparatus according to claim 4, wherein the measurement means performs measurement in relation to the measurement positions of the sample when the measurement positions of the sample are indicated by the input means in a state in which the optical image of the sample, the measurement positions of the sample, the absolute value of the stress, the positive and negative stress, and the direction of application of the stress are visually displayed on the display.

6. The X-ray stress measurement apparatus according to claim 1, wherein the image formation means:
  displays the measurement positions of the sample by ring-shaped dots;
  displays the absolute value of the stress by the size of the ring-shaped dots;
  displays positive and negative stress using a difference in color of the ring-shaped dots; and
  displays the direction of application of the stress using direction notation symbols.

7. The X-ray stress measurement apparatus according to claim 6, wherein the measurement means performs measurement in relation to the measurement positions of the sample when the measurement positions of the sample are indicated by the input means in a state in which the optical image of the sample, the measurement positions of the sample, the absolute value of the stress, the positive and negative stress, and the direction of application of the stress are visually displayed on the display.

8. The X-ray stress measurement apparatus according to claim 1, wherein the image formation means:
  displays the measurement positions of the sample using an intersection of a pair of mutually orthogonal arrows;
  displays the absolute value of the stress using the length of the arrows;
  displays positive and negative stress using a difference in color of the arrows; and
  displays the direction of application of the stress using the orientation of the arrows.

9. The X-ray stress measurement apparatus according to claim 8, wherein the measurement means performs measurement in relation to the measurement positions of the sample when the measurement positions of the sample are indicated by the input means in a state in which the optical image of the sample, the measurement positions of the sample, the absolute value of the stress, the positive and negative stress, and the direction of application of the stress are visually displayed on the display.

10. The X-ray stress measurement apparatus according to claim 1, further comprising distinctive point display means, the distinctive point display means having a plurality of types of parameters for defining whether the sample is distinctive, and performing a distinctive point display for displaying a distinctive point at a corresponding measurement position when the measurement value of the parameters is a value expressing distinctiveness.

11. The X-ray stress measurement apparatus according to claim 10, wherein the measurement means performs measurement in relation to the measurement positions of the sample when the measurement positions of the sample are indicated by the input means in a state in which the optical image of the sample, the measurement positions of the sample, the absolute value of the stress, the positive and negative stress, and the direction of application of the stress are visually displayed on the display.

12. The X-ray stress measurement apparatus according to claim 1, wherein the measurement means performs measurement in relation to the measurement positions of the sample when the measurement positions of the sample are indicated by the input means in a state in which the optical image of the sample, the measurement positions of the sample, the absolute value of the stress, the positive and negative stress, and the direction of application of the stress are visually displayed on the display.

* * * * *